United States Patent [19]

Kawagoe et al.

[11] Patent Number: 4,995,727
[45] Date of Patent: Feb. 26, 1991

[54] COMPACT DIFFUSION LIGHT MIXING BOX AND COLORIMETER

[75] Inventors: Nobukazu Kawagoe; Masami Sugiyama; Masahito Inaba, all of Osaka, Japan

[73] Assignee: Minolta Camera Kabushiki Kaisha, Osaka, Japan

[21] Appl. No.: 195,962

[22] Filed: May 19, 1988

[30] Foreign Application Priority Data

| May 22, 1987 | [JP] | Japan | 62-125365 |
| May 30, 1987 | [JP] | Japan | 62-137458 |
| Jun. 5, 1987 | [JP] | Japan | 62-141041 |
| Jun. 5, 1987 | [JP] | Japan | 62-141042 |

[51] Int. Cl.$^5$ .................. G01J 3/51; G01J 1/18
[52] U.S. Cl. .................. 356/402; 250/228; 356/236; 362/355
[58] Field of Search ........... 356/402, 236, 243, 250; 250/228; 362/355

[56] References Cited

U.S. PATENT DOCUMENTS

| 4,047,032 | 9/1977 | Judge et al. | 356/243 X |
| 4,658,131 | 4/1987 | Stark | 356/236 X |
| 4,673,818 | 6/1987 | Guerra | 350/228 X |

FOREIGN PATENT DOCUMENTS

| 0177861 | 4/1986 | European Pat. Off. | 356/236 |
| 57-69222 | 4/1982 | Japan . |
| 58-132632 | 8/1983 | Japan . |
| 59-92318 | 5/1984 | Japan . |
| 59-231427 | 12/1984 | Japan . |

OTHER PUBLICATIONS

Japanese Industrial Standard Z8722 Documents Issued by Japan Illumination Committee.

Primary Examiner—Vincent P. McGraw
Attorney, Agent, or Firm—Price, Gess & Ubell

[57] ABSTRACT

A colorimeter comprises a light source, a mixing box formed of non-coated light diffusing surface manufactured by molding sintering white ceramics or white resin for diffusing and reflecting light from the light source to guide the same to a sample, first light receiving means for receiving light reflected from the sample when light is emitted from the light source, and second light receiving means for receiving light other than the light reflected from the sample emitted from the light source.

11 Claims, 13 Drawing Sheets

COMPACT DIFFUSION LIGHT MIXING BOX AND COLORIMETER

BACKGROUND OF THE INVENTION

1. Field of the Invention

The present invention relates generally to a light mixing box and a colorimeter employing the same and, more specifically, it relates to a light mixing box employing white ceramics or white resin and a colorimeter employing the same.

2. Prior Art

Conventionally, a reflector for a flash apparatus has been developed mainly for photography in order to enhance reflectance and directivity by using a mirror surface of a parabolic curve. Meanwhile, diffuse illumination has been required in various fields. The diffuse illumination generally lowers the illumination efficiency and makes the illuminating apparatus tend to be large. In some fields, a compact diffuse illumination is required. One of such fields is that of a colorimeter. A normal colorimetry is effected by using a spectrophotometer. However, the spectrophotometer is a large and expensive apparatus, which can not be readily used in general. Therefore, a handy type colorimeter has been developed and used widely in the fields of color conditioning in manufacture, quality control of printed matters, medical inspection, cosmetology, and the like. The object to be measured must be illuminated by the ideal diffused light in order to enhance the precision of colorimetry. As for a measuring apparatus used in the field, measurement should be carried out in a short time period with bright illumination in order to avoid influence of outer light. Therefore, a flash apparatus is used as a light source. A reflector, conventionally a mirror surface reflector, is used therewith to enhance the efficiency of light. As the discharge tube such as xenon tube is used in the flash apparatus, the discharging path in the tube changes every time. This means that the position of the light source moves every time.

FIG. 1 shows a reflector 1 having a paraboloid revolution, and a flash light source 2. The central axis O of the flash light source 2 is located at the focal point of the paraboloid curve of the reflector 1. The light path of the flash light source changes every time dependent on the distribution of excitation of the gas filled in the flash light source. In FIG. 1, the thick solid line shows the path of the light generated from the point A, while the dotted line shows the path of the light generated from the point B. The flash light source 2 can not be regarded as a point source in relation to the size of the reflector 1. Therefore, when the light generated from the light source 2 is reflected by the reflector 1, the reflected light from the point A differs from the reflected light from the point B, depending on the direction of emission, as shown in FIG. 2. For example, in the case of the light reflected in the direction of φ, the amount of the reflected light becomes as shown by a, c and b, corresponding to the points of light generation A, O, B, respectively. Therefore, the fluctuation in the flash light source causes variation of light amount in the emitting direction of the reflected light, affecting the measurement.

In order to solve the above problem, a diffuse illumination light source is implemented by providing a transmitting diffusion plate such as white acryl plate, frosted glass plate, and the like in front of the light source in a handy type colorimeter shown in FIG. 3. However, the amount of illumination is decreased due to the transmittance characteristics of the diffusion plate. For example, according to the spectral transmittance characteristics of the white acryl plate, the transmittance of the wavelength less than 400 nm is low, so that when it is employed as a light source of a colorimeter, the resolution of blue will be degraded. If the white acryl plate is placed near the flash light source, the plate may possibly be deformed or the color of the plate may be changed due to the power of the light source.

Conventionally, in the field of integrating sphere, powder coatings of barium sulfate, zinc oxide and magnesium oxide are used as materials having no wavelength selectivity, high reflectance and high diffusiveness. However, these materials have problems in the surface adhesiveness and moisture resistance, so that they are not the optimum material for a reflector in the flash apparatus.

As an another example of the prior art, a conventional integrating sphere employed in the colorimeter or other measuring apparatuses is shown in FIG. 4. A perfect diffuse surface 22 having high reflectance and no wavelength selectivity is formed by applying powder of zinc oxide, magnesium oxide, barium sulfate or the like on the inner wall surface of the upper hemisphere 21a and the lower hemisphere 21b. Since the adhesiveness of the powder is weak, it may peel off when an impact is applied thereon. Therefore, the integrating sphere should be carefully handled. A binder may be mixed with the powder to be applied in order to enhance the adhesiveness. However, the performance of the integrating sphere is degraded due to the spectral reflectance characteristics (especially wavelength selective absorption) of the material serving as the binder, and the binder may be turned yellow by the ultraviolet rays. In manufacturing, the reflected layer must be thick in order to enhance the reflectance. Therefore, a number of layers of the powder must be applied to the metal surface. This makes the manufacturing difficult and it is not suitable for massproduction.

FIG. 5 shows a conventional integrating sphere used in a handy type colorimeter which is made in consideration of the impact resistance. Since it is a handy type, the integrating sphere must have high impact resistance and a simple and compact structure. Therefore, the inner surface 29 of the sphere 21 is coated with a delustered type white coating film which is strong. According to the characteristic of the spectral reflectance of the white coating of the inner surface 29, it appears that the reflectance in the wavelength shorter than 420 nm is degraded. Therefore, it does not satisfy the required quality of the integrating sphere, i.e., "it should have reflectance characteristics having no wavelength selectivity". In addition, since the diffusion reflectance characteristics of the delustered white coating of the inner surface 29 differs entirely from the perfect diffusion, the characteristics must be compensated by a diffusion transmitting plate 30 for improving diffusion characteristics. The diffusion transmitting plate reduces the intensity of the illumination.

In a simple integrating sphere employed in a conventional handy type colorimeter and the like, delustered white coatings are employed because of the strength of the coat. However, in that case, the reflectance characteristics of the light in the range of wavelength shorter than 400 nm is inferior, so that required amount of light for illuminating the sample can not be obtained. In a normal integrating sphere, white powder of zinc oxide, magnesium oxide, barium sulfate or the like is applied. Although the reflectance characteristics of the same is superior, it is weak against impact.

As a further example of the prior art, a conventional integrating sphere in a colorimeter of diffused illumination vertical receiving system is shown in FIG. 6, which integrating sphere has the function of removing specularly reflected light.

The vertical light receiving system means that "the angle of inclination of the light reflected from the sample surface from the perpendicular of the sample surface is no more than 10°". The system shown in FIG. 6 is the 8° light receiving system in accordance with the above definition. In the example shown in FIG. 6, the light from the light source 48 is diffused by the integrating sphere 41 so as to uniformly irradiate the sample 43 and the direct light from the light source 48 is prevented from irradiating the sample 43 by a baffle 49B. The light receiving opening A is inclined by 8° from the vertical direction so as not to receive the specularly reflected light from the sample. A light trap 41A which absorbs specularly reflected light is provided in the direction of reflection. The advantage of this system is that the specularly reflected light from the sample is perfectly avoided, since the light receiving opening A is positioned in relation to the opening portion of the light trap 41A so as not to receive the specularly reflected light. A first disadvantage of the system shown in FIG. 6 is that the opening A can receive no reflected luminous flux in the vertical direction (0° direction) of the sample 43, but it can receive the luminous flux in the direction inclined by 8° from the vertical direction, so that the information of the light in the vertical direction (0° direction), which is originally desired, can not be obtained. A second disadvantage is that in order to obtain the reflected light from the specified region of the measured sample 43 through the light receiving opening A, a collimate lens K must be used and a light trap is required. When a collimate lens K is employed, there are various disadvantages. For example, it is difficult to make the apparatus compact, the assembly becomes troublesome, the apparatus becomes expensive, and it is not suitable for a handy type apparatus.

The center of the light receiving opening A may be provided at the top point P of the integrating sphere so as to place the same in the perfect vertical direction to the measured sample 43, whereby only the vertical reflected light from the sample is measured by a collimate lens. In this structure, since the light receiving opening is provided, there is no wall of the integrating sphere which is the source of the specularly reflected light from the sample to the opening. However, since the reflected light from the sample and from the vicinity of the sample is reflected by the collimate lens and directly irradiates the sample again, the specularly reflected light from the sample 43 is mixed with the measuring light, causing errors in the measurement.

A conventional example of an integrating sphere in a handy type diffusion illumination vertical light receiving system colorimeter (chromameter) is shown in FIG. 7. It differs from the integrating sphere of FIG. 6 in the following points. Namely, the region of the sample 43 to be measured is limited by a cylinder 42 whose axis is the central line of the limiting opening B. The collimate lens K of FIG. 6 is eliminated. The integrating sphere 41 is divided into the upper and lower chambers. A diffusion transmitting plate 50 is provided between two chambers to improve the diffusion illuminating characteristics. In this system, the light illuminating the sample has less orientation but a large quantity of light. However, as for the light emitted from the region (K—K') of the diffusion transmitting plate 50 and reflected on the sample surface which can be seen from the light receiving opening A, the light enters the light receiving opening A as a specularly reflected light from the sample. Therefore, the specularly reflected light from the sample can not be eliminated.

A still further example of the prior art is shown in FIG. 8, in which a reference opening C is provided at a position close to the measuring opening A in order to take the reflected light from the inner surface D of the integrating sphere 51 adjacent to the sampling opening S of the integrating sphere 51. A collimate lens K is provided on the monitoring light axis which goes through the center of the reference opening C and the center of the region D of the wall surface of the integrating sphere 51, so that only the light from the region D of the wall surface is monitored. Therefore, only the light parallel to the light axis of the collimate lens K passes through the collimate lens K to reach the monitor light receiving sensor S2, although the reference surface D is illuminated from all the directions in the integrating sphere 51 and reflects light to all the directions.

Consequently, the amount of the monitor light is small and the S/N ratio of the light measurement is low, so that the variation of the light source can not be effectively corrected. Since the reference opening is approximately opposite to the sampling opening, a collimate lens is used so that the reflected light from the sampling opening do not enter the reference opening. The region of the inner surface of the integrating sphere which is viewed from the collimate lens through the reference opening should not be overlapped with the sampling opening. Therefore, the smaller the apparatus becomes, the smaller becomes the region of the inner surface of the integrating sphere viewed from the reference opening, whereby the monitoring light measurement becomes difficult.

An optical fiber may be used instead of the collimate lens. However, since the optical fiber transmits only light emitted in a certain range of angle, and every optical fiber has different range of light receiving angle. Therefore, in order not to receive the light from the surface to be measured, considerable margin is required in design for positioning and for adjusting the direction of the light axis of the optical fiber. Consequently, it is difficult to make the apparatus compact. A cylinder which limits the range of measurement may be provided projecting in the integrating sphere from the reference opening so as to prevent entrance of the light from the surface to be measured. However, in this case, the integrating sphere becomes far apart from the ideal shape and the light amount can be increased.

SUMMARY OF THE INVENTION

One object of the present invention is to provide a long life reflector of a flash apparatus which is independent from the fluctuation of the light source in order to eliminate instability of illumination due to the fluctuation of the light source.

Another object of the present invention is to provide an integrating sphere which eliminates the above described problems and which has good reflectance characteristics in wide range of wavelength.

A further object of the present invention is to maintain an illuminating optical system of a diffusion illumination.vertical light receiving system for eliminating the specularly reflected light, to perfectly eliminate the specularly reflected light from the sample, to obtain the illumination light amount as much as possible, and to make the integrating sphere compact by removing any collimate lens or the like.

A still further object of the present invention is to increase the light amount of the monitoring light and to make the integrating sphere compact by taking the light reflected from the range as wide as possible of the inner wall of the integrating sphere without changing the shape and the inner structure of the integrating sphere.

According to the first aspect of the present invention, a colorimeter comprises: a light source; a mixing box of a non-coated light diffusing surface made by molding.-sintering of white ceramics or white resin to diffuse and reflect the light from the light source to guide the same to the sample; first light receiving means for receiving light reflected from the sample when the light source emits light; and second light receiving means for receiving light other than the light directly reflected from the sample when the light source emits light.

According to the second aspect of the present invention, a colorimeter of diffusion illumination.vertical light receiving system comprises: a mixing box; and a cylinder projecting in the mixing box from the upper surface of the mixing box, with the cylinder having an opening for limiting the region to be measured at the opening portion of the projecting end in the mixing box, a light receiving opening provided therein, and a collar portion provided at the outer periphery thereof, the inner surface of the cylinder to the light receiving opening being subjected to the light absorbing treatment, and a surface of said collar portion which is opposed to the sample being subjected to the light absorbing treatment.

According to the third aspect of the present invention, the mixing box consists of a non-coated light diffusing surface made by molding.sintering of white ceramics or white resin.

According to the fourth aspect of the present invention, a reflector for a flash apparatus consists of a concave non-coated light diffusing surface formed by molding.sintering of white ceramics or white resin.

According to the fifth aspect of the present invention, in a colorimeter of a diffusion illumination.vertical light receiving system employing a mixing box, a surface for receiving a monitor light is provided directly adjacent to a sampling opening on the inner surface of the mixing box.

These objects and other objects, features, aspects and advantages of the present invention will become more apparent from the following detailed description of the present invention when taken in conjunction with the accompanying drawings.

DESCRIPTION OF THE PREFERRED EMBODIMENTS

Embodiment 1

Figure 9:
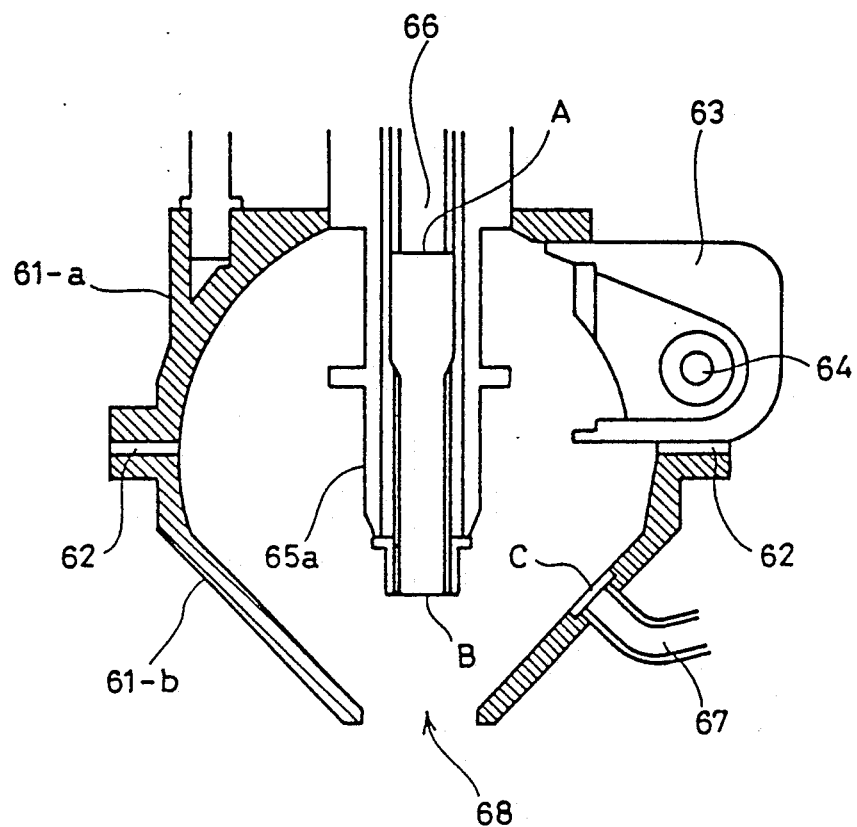
FIG. 9 is a vertical sectional view of one embodiment of the present invention.

FIG. 9 shows an embodiment of the present invention which is applied to a handy type colorimeter of a diffusion illumination.vertical light receiving system. The reference numeral 61 denotes an integrating sphere for realizing perfect diffusion illumination, constituted by coupling an upper hemisphere 61-a and a lower hemisphere 61-b. Both hemispheres 61-a and 61-b are formed by molding.sintering white resin (for example, tetrafluoroethylene) or white ceramics (for example, aluminum oxide or boron nitride). The reference numeral 62 denotes a cushion of silicon rubber interposed between the upper hemisphere 61-a and the lower hemisphere 61-b as a buffer when the hemispheres are coupled. The reference numeral 63 denotes a reflector provided in the side surface of the upper hemisphere 61-a, which is formed of the same material as the hemispheres 61-a and 61-b. 64 denotes a xenon tube which is a flash generating light source. 65 denotes a cylinder determining the range of measurement of the sample surface. 66 denotes a light receiving optical fiber, the light receiving end of which is placed in a deep portion of the cylinder 65. 67 denotes an optical fiber which guides light for monitoring illumination to a photosensitive element for monitoring. 68 denotes a sample opening of the integrating sphere 61 which is pressed onto the sample. The xenon tube 64 is exposed to the inside of the integrating sphere 61, and surrounded by the reflector 63 whose reflection axis is turned slightly upward, so that the light does not directly irradiate the sample surface.

The measurement of color starts with locating the sample opening 68 at the sample surface. The light reflected from the sample passes through an optical fiber 66 and is guided to a photodetector, not shown, for signal processing. In this measurement, since the discharge path of the flash discharge tube changes every time, the substantial position of the light source changes. However, since the integrating sphere is formed with an inner surface capable of perfect diffusion illumination, the sample illumination do not fluctuate dependent on the change of position of the light source. Therefore, the sample can be illuminated by a stable light amount of illumination.

Figure 10:
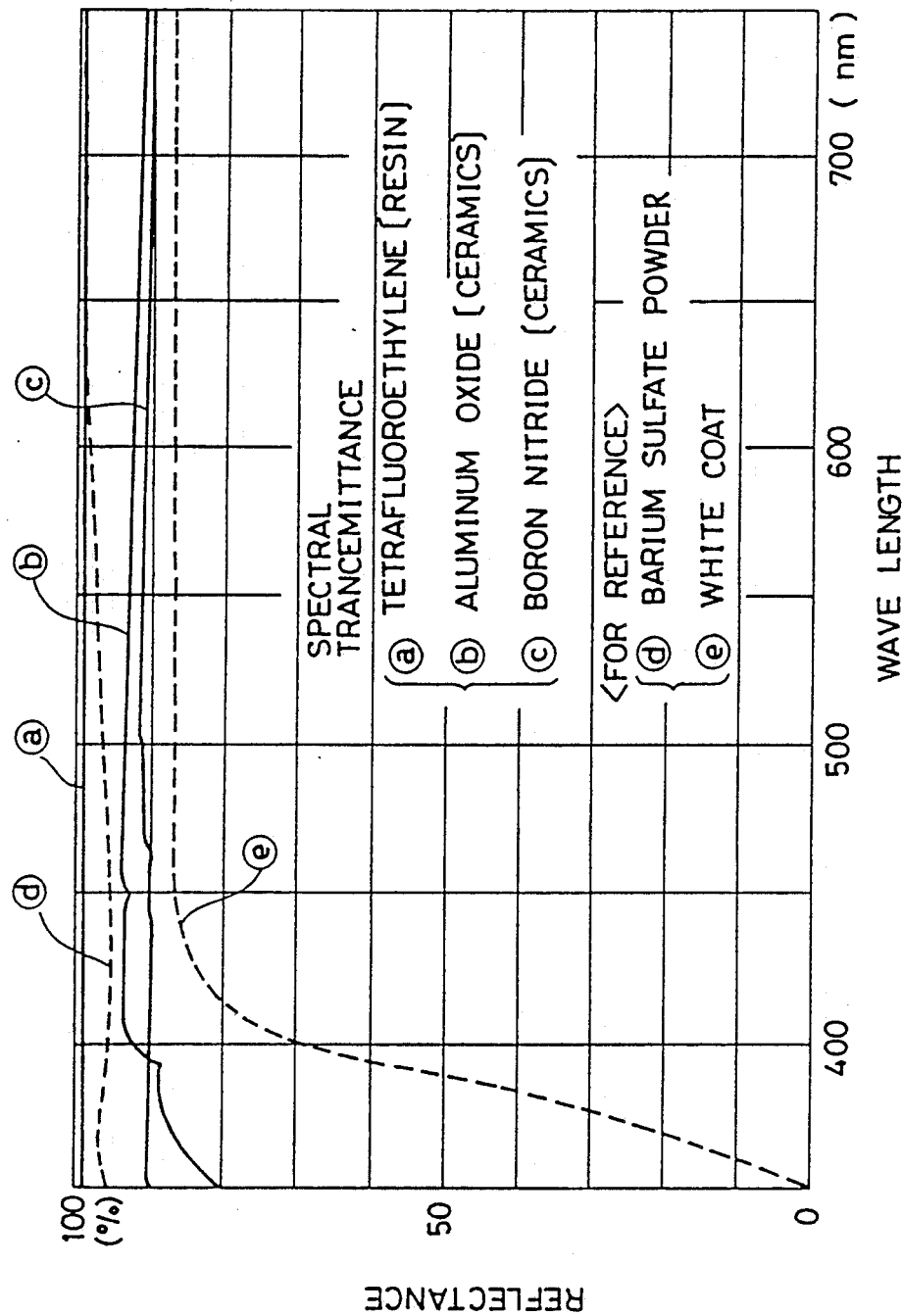
FIG. 10 is a graph showing the relation between the wavelength and the reflectance of various materials.
Figure 11:
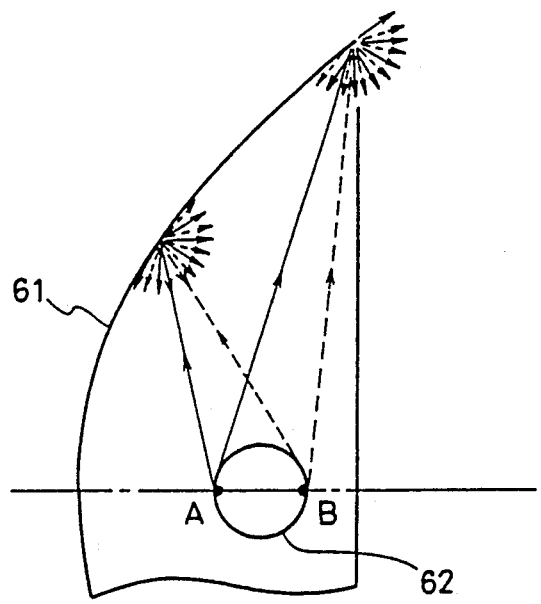
FIG. 11 illustrates the reflection of light emitted from the points A and B in the embodiment of FIG. 9.
Figure 12:
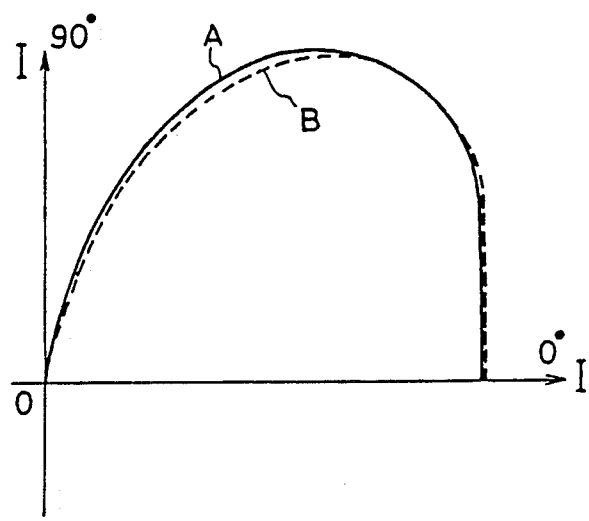
FIG. 12 is a graph showing the relation between the direction of light emitted from the points A and B and the amount of light in the embodiment of FIG. 9.

The integrating sphere 61 is manufactured by pressure molding powder of (1) tetrafluoroethylene, (2) aluminum oxide, (3) boron nitride, and the like and by sintering the same thereafter. The spectral reflectance characteristics thereof are shown in FIG. 10. Since the manufacturing is effected by molding.sintering, these materials have superior moisture resistance, heat resistance, impact resistance as well as high insulation. Therefore, these materials are suitable for the insulator of a flash generating light source which is subjected to a high voltage. FIG. 12 shows the relation between the light amount and the direction of light emitted from the points A and B of the flash generating light source 62 to the parabolic reflector as shown in FIG. 11. The sintered material employed in the reflector 61 of the present invention has a perfect diffusion reflectance characteristics in which there is only a little wavelength selectivity in the visible range as shown in FIG. 10, so that the light emitted from the point A and the light emitted from the point B reflect in approximately the same way as shown in FIG. 12. Therefore, even if the light emission is unstable in the light source 62, the light reflected by the reflector 61 is free from fluctuation.

Although the diffusion reflecting surface of the integrating sphere manufactured by molding.sintering of the materials such as (1), (2) and (3) described above has reliable diffusion reflectance characteristics with the molded surface as it is, the surface of the mold may be provided with concaves and projections so as to control the diffusion characteristics of the finished diffusion reflecting surface.

In accordance with this embodiment, since the reflecting surface of the reflector is a diffusion reflecting surface, a stable light source can be obtained and the measuring precision of the colorimeter and the like is considerably enhanced. In addition, by manufacturing the reflector with materials having superior diffusiveness and high resistance against environmental influences, a long life reflector for a flash apparatus can be provided.

Since the reflecting surface of the integrating sphere is a diffusion reflecting surface made of a material having flat spectral characteristics in the visible range and high reflectance, a stable illumination for the sample can be provided in the wide range of wavelength and the measuring precision of the colorimeter and the like is considerably enhanced. In addition, since the integrating sphere is manufactured with materials having high resistance against environmental influences, a long life integrating sphere can be provided.

Embodiment 2

Figure 13:
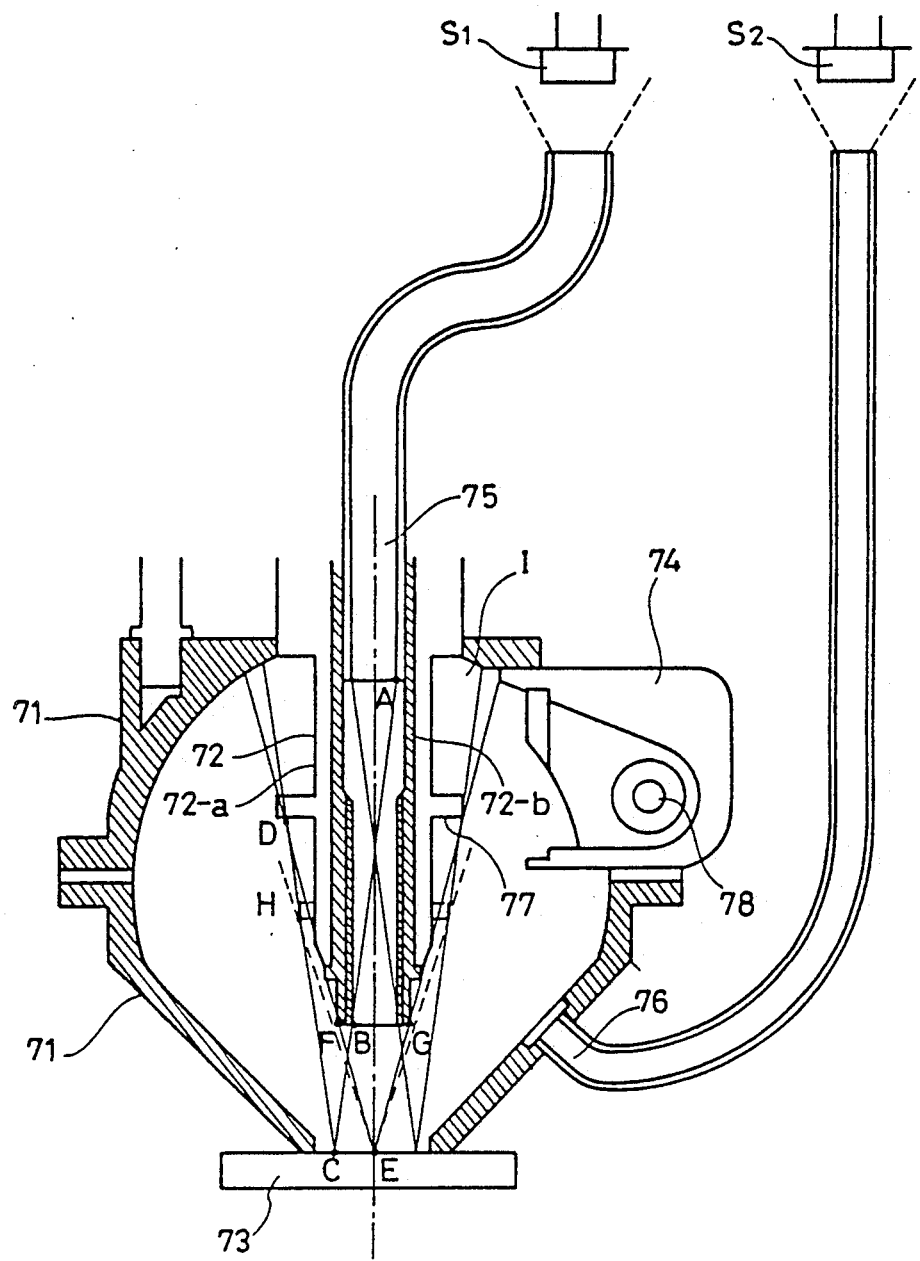
FIG. 13 is a vertical sectional view of another embodiment.

FIG. 13 shows one embodiment of the integrating sphere in accordance with the present invention. In FIG. 13, the reference numeral 71 denotes the integrating sphere. The numeral 72 denotes a cylinder provided for limiting the measurement region, which is inserted downward from the upper surface of the integrating sphere 71 to a position slightly lower than the center of the integrating sphere 71, with the lower end thereof being opened as a limiting opening B. In the cylinder 72, a light receiving optical fiber 75 is held at a position where the light receiving end thereof is aligned with the upper surface of the integrating sphere 71. The reference numeral 73 denotes a sample to be measured. The reference numeral 74 denotes a reflector provided in the side surface of the integrating sphere 71, by means of which the light from the light source 78 is emitted uniformly in the integrating sphere 71. The light receiving optical fiber 75 guides the reflected luminous flux from the sample 73 to a spectral sensor S1 for measuring the sample. The numeral 76 denotes a light receiving optical fiber which guides the luminous flux to a spectral sensor S2 for measuring the light source which measure the fluctuation of the light source 78. The numeral 77 denotes a collar provided around the outer periphery of the cylinder 72 in order not to present the specularly reflected light.

The light from the source 78 is reflected by the reflector 74 to enter the integrating sphere 71. The light entered the integrating sphere 71 is diffused and reflected by the inner surface of the integrating sphere 71 to be the non-directional illumination, whereby the sample 73 is illuminated from all direction. In order to prevent the specularly reflected light from the surface of the sample from entering the lower opening portion A of the light receiving optical fiber 75 which serves as a light receiving opening, the collar 77 is provided on the outer periphery of the cylinder 72 to limit the angle of irradiation of the luminous flux to the sample 73. The surface of the collar 77 which is opposed to the sample is painted black to absorb light. Therefore, the specularly reflected light of the sample surface does not enter the light receiving opening A.

The cylinder 72 comprises an outer cylinder 72-a and an inner cylinder 72-b. The outer cylinder 72-a is made of white ceramics (for example, aluminum oxide or boron nitride) having superior diffusion reflectance characteristics, with which the collar 77 is integrally molded.sintered. The surface of the collar 77 opposed to the sample is optically black painted to absorb light in order not to present the specularly reflected light. Although it has a superior diffusion reflectance characteristics, the outer cylinder is translucent, so that the cylinder 72-b is inserted in order to prevent light from entering the cylinder. The inner cylinder 72-b is formed of aluminum. If the inner surface of the cylinder were specularly finished, the limiting opening B would substantially serve as a light receiving opening A. Therefore, a thread for preventing inner surface reflection is provided on the inner wall of the cylinder 72-b, and the inner wall is optical black painted to absorb light. An outer wall portion of the cylinder 72-b exposed to the integrating sphere is also painted black to absorb light. The molded surface of the white ceramics of the outer cylinder 72-a has superior reflectance characteristics, no wavelength selectivity and superior diffusion reflectance, whereby the effect of integrating of the integrating sphere is considerably enhanced.

Although the outer cylinder and the collar for preventing the specularly reflected light are formed of ceramics by solid molding in the above example, the outer cylinder may be divided into an upper cylinder, a collar and a lower cylinder. A white resin (tetrafluoroethylene, etc.) may be used instead of ceramics.

The cylinder 72 may be formed integrally and powder of barium sulfate, zinc oxide and the like which is generally used for the inner wall of the integrating sphere may be applied to the outer wall surface thereof except a portion painted optically black.

A black treated portion I for preventing specularly reflected light may be provided on the inner wall surface of the integrating sphere instead of the collar 77. However, the proportion of the black surface area to the total area of the inner surface of the integrating sphere 71 is strongly related to the integrating effect of the integrating sphere and to the light amount of the illumination to the sample 73. The proportion of the area occupied by the surface for preventing specularly reflected light should be as small as possible. When we compare the area of the black treated portion I on the wall surface of the integrating sphere 71 with the area of the collar 77 in accordance with the present invention, the collar 77 can be formed with smaller area and the loss of the effective area in the integrating sphere can be more reduced. The shorter the distance between the collar 77 and the bottom edge of the cylinder 72, the smaller becomes the area for removing the specularly reflected light. In view of the foregoing, the present embodiment is more effective.

In the specularly reflected light entering the light receiving opening A of the light receiving optical fiber 75, the beam passing through an outer periphery of the opening at the end B of the inner wall of the cylinder 72 and an outer periphery of the light receiving opening A of the light receiving optical fiber 75 forms a maximum incidental angle. An imaginary specular light beam in relation to the path A-B reflected by the surface of the sample 73 could be denoted by C-D. All the specularly reflected light beams entering the light receiving optical fiber 75 are included in a truncated cone with the said light beam C-D being a ridge line. The point D of the imaginary beam of the specularly reflected light which could enter the optical fiber 75 must be placed on the lower surface of the collar 77 for preventing the specularly reflected light. The minimum incidental angle of the light being measured is defined by the inner diameter of the cylinder 72 and by the distance between the bottom end of the cylinder 72 and the light receiving opening A. Preferably, the angle can be determined in the angle range of 0° to 10° corresponding to the specification of the apparatus.

Among the light beams having a minimum incidental angle in the range of measurement, the light beams E-G and E-F reflected at the center E and being in tangential contact with the outer wall of the cylinder 72 have the largest incidental angle. Reduction of the incidental angle of the light beams E-G and E-F means reduction of the incidental angle of the light beams in the range of measurement. The point D is the intersection of the light beam E-F which is the tangent line to the point F of the outer wall of the cylinder 72 and the light beam C-D which have the maximum incidental angle among the specularly reflected light beams. If the collar 77 for preventing the specularly reflected light was provided near the bottom end of the cylinder 72, the collar 77 would intercept the light beam E-F-D, and the beam having the maximum incidental angle reflected at the point E would be E-H having larger incidental angle.

In the foregoing, for most effectively realizing the present invention, the outer periphery of the collar 77 should be placed outer than the specularly reflected light beam C-D which forms the maximum incidental angle about the central line of the cylinder 72, and inner than the beam E-F-D of maximum incidental angle reflected at the center E so as to be as close as possible to the point D which is the intersection of said two light beams. Namely, the collar 77 should be designed such that the point D is located on the lower surface thereof.

Figure 14:
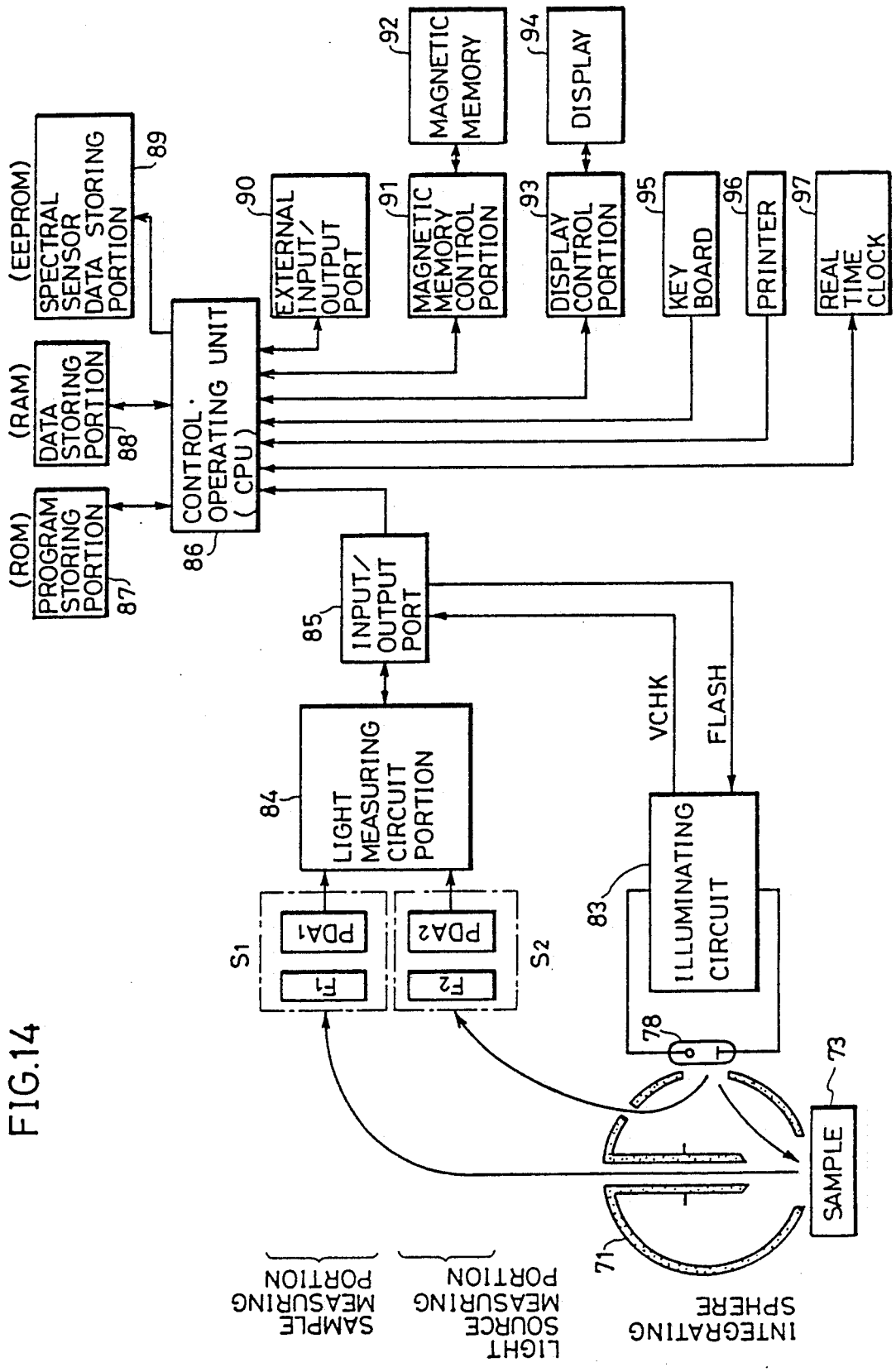
FIG. 14 is a block diagram showing whole structure of the embodiment of FIG. 13.

FIG. 14 shows a color measuring circuit of one embodiment of the colorimeter employing the integrating sphere of the present invention. The light source which is a pulse xenon lamp is controlled by the illuminating circuit 83. S1 is a spectral sensor for detecting the light reflected from the sample 73 in the direction of 0°. A spectroscope F1 is provided in the spectral sensor S1, which forms a pair with a photodetector PDA1 which is also provided in the spectral sensor S1, wherein 40 sets of band path filters (one of the components of the spectroscope F1) and silicon photodiodes (one of the components of the spectroscope PDA1) are arranged in parallel with each other. The light passed through the band path filters is received by the silicon diodes, so as to detect the light of short wavelength to long wavelength. S2 denotes a spectral sensor for measuring the light source, which detects the luminous flux from the light source 78 having short to long wavelength by 40 sets of band path filters and silicon photodiodes in the same manner as the spectral sensor S1. 84 denotes a light measuring circuit portion which integrates and A/D converts the detected signal obtained from the spectral sensors S1 and S2, for every detected wavelength.

The signal which is A/D converted by the light measuring circuit portion 84 is transmitted to the control.operating unit (CPU) 86 through an input/output port 85. The control.operating unit 86 is a central processing unit which controls and operates the whole system. The control.operating unit 86 is connected to a program storing portion 87 which stores programs to be executed by the control.operating unit 86; a data storing portion 88 for storing the operation data, the states of the system, and so on; a spectral sensor data storing portion 89 for storing the wavelength detected from the spectral sensor S1 and S2 and constants for correction, and so on; an external input/output port 90 for exchanging data with external devices such as external personal computers and the like; a magnetic memory device control portion 91 for controlling a magnetic memory device 92 such as a floppy disk device, a hard disk device, and the like; a display control portion 93 for controlling display portion 94 comprising a liquid crystal device, CRT or the like; a keyboard 95; a printer 96; and a real time clock 97 which indicates the real time, all of which are controlled by the control.operating portion 86.

The operation of measurement by the above colorimeter will be described in the following. When a sample 73 is placed at the sample opening of the integrating sphere 71 and a measuring key provided on the keyboard 95 or a measuring key provided in the light measuring circuit 84 is pressed, the control operating unit 86 starts the measuring operation in accordance with the measuring program in the program storing portion 87.

The control operating unit 86 checks a signal VCHK through the input/output port 85. The signal indicates whether the illuminating circuit 83 is ready or not for flashing the pulse xenon lamp 78. When the illuminating circuit 83 is ready, the control operating unit 86 transmits a measurement start signal to the light measuring circuit portion 84 through the input/output port 85 and, simultaneously, it transmits a FLASH signal to the illuminating circuit 83 to flash the pulse xenon lamp 78. The white light emitted from the pulse xenon lamp 78 irradiates the integrating sphere 71, and then uniform diffused light is made by the integrating effect. A portion of the light enters the spectral sensor S2 for measuring the light source. The remaining other portion of the light diffused illuminates the sample 73, and the light reflected from the sample 73 enters the spectral sensor S1 for measuring the sample. The photoelectric current proportional to the energy of each detected wavelength of the light received by the sensors S1 and S2 is inputted to the light measuring circuit portion 84. The current from each silicon photodiode in the sensor S1 and S2 is integrated and A/D converted corresponding to every set wavelength. The resulting value is inputted to the control.operating unit 86 through the input/output port 85. The proportion of the A/D converted value corresponding to the detected light to the value of standard reference data in the storing portion 88 is calculated for evaluating the absolute value of the detected light. The standard reference data has been obtained by measuring a reference compensating plate instead of the sample prior to the measuring of the sample. The obtained proportion is multiplied by the absolute reflectance of the standard is multiplied by the absolute reflectance of the standard reference data to obtain the reflectance of the sample. The influence of the fluctuation of the light source on the reflectance of the sample is compensated for by the proportion of the A/D converted value of the light from the reference compensating plate being measured. The resulting value is stored in the data storing portion 88 as the absolute value of the spectral reflectance of the sample. The calculation for display and color operation are carried out on the spectral reflectance data of the sample 73 stored in the data storing portion 88 in accordance with the designation of the display mode (for example, graphic display of the reflectance, graphic display of color, display of density, etc.) or with the designation of the color specification. The result is transmitted to the display control portion 93 to be displayed on the display portion 94.

According to the present embodiment, the specularly reflected light can be eliminated without reducing the light amount of illumination, whereby the precision of measurement is considerably enhanced. Embodiment 3

Figure 15:
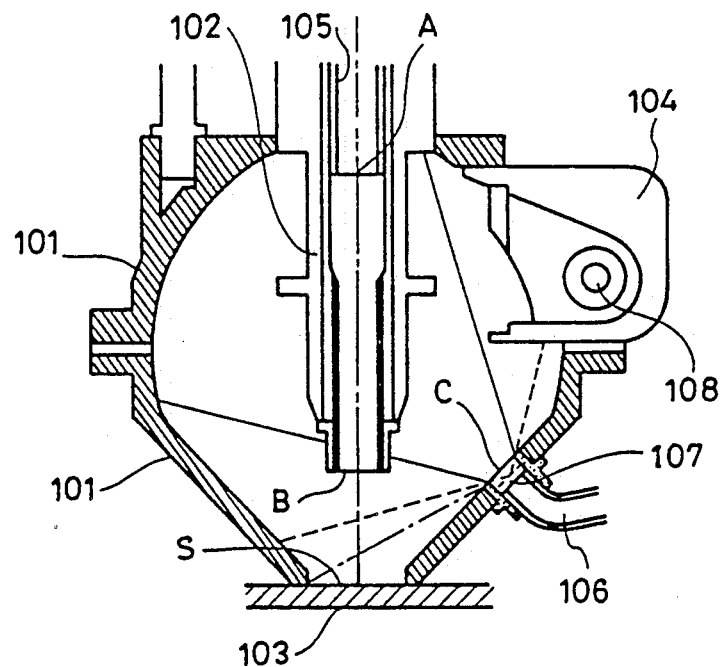
FIG. 15 is a vertical sectional view of a further embodiment.

FIG. 15 shows one embodiment of the colorimeter in accordance with the present invention. In FIG. 15, the reference numeral 101 denotes an integrating sphere. The numeral 102 denotes a cylinder provided for limiting the region to be measured, which is inserted downward from the top surface of the integrating sphere 101 to a position slightly lower than the center of the integrating sphere 101, with the lower end being open as a limiting opening B. In the cylinder, an optical fiber 105 for receiving light is held such that the light receiving end thereof is positioned approximately aligned with the upper surface of the integrating sphere 101. The numeral 103 denotes a sample to be measured and 104 denotes a reflector provided in the side surface of the integrating sphere 101, by means of which the light emitted from the light source 108 uniformly irradiates the integrating sphere 101. The optical fiber 105 for receiving light guides the reflected luminous flux from the sample 103 to the spectral sensor (not shown) for measuring the sample. The numeral 106 denotes an optical fiber which guides the luminous flux to a spectral sensor (not shown) for monitoring the light source, which sensor measures the fluctuation of the light source 108. The optical fiber 106 is provided in a reference opening C provided adjacent to the sample opening S at the lower part of the integrating sphere 101. The numeral 107 denotes a light diffusing plate provided in front of the light receiving surface of the optical fiber 106 for widening light receiving.

The light emitted from the light source 108 is reflected by the reflector 104 to irradiate the integrating sphere 101. The light entered the integrating sphere 101 is diffused and reflected in the integrating sphere 101 to be an illumination light having no directivity. The illumination light irradiates the sample 103 from all directions. Since the reference opening C is provided adjacent to the sample 103, approximately the same light illuminating the sample 103 enters the reference opening C. A diffusing plate 107 is provided at a position in the reference opening C where the direct light from the sample 103 does not enter. Light absorbing treatment is carried out on the cylindrical inner surface of the reference opening C. The light transmitted through the diffusing plate 107 passes through the optical fiber 106 to be measured by the spectral sensor for monitoring the light source. If the diffusion transmitting plate 107 were not used, the light in the range defined by the solid lines (the range defined by the light receiving angle of the optical fiber 106) could be utilized as the light amount entering the optical fiber 106. The diffusion transmitting plate 107 is used in this embodiment, so that the amount of light to be received can be enhanced since light from the wider range defined by the dotted lines can be utilized. Since the optical fiber 106 is employed, the sensor for receiving monitoring light can be freely located, whereby the monitor light can be received without any projection provided near the measuring opening.

Figure 1:
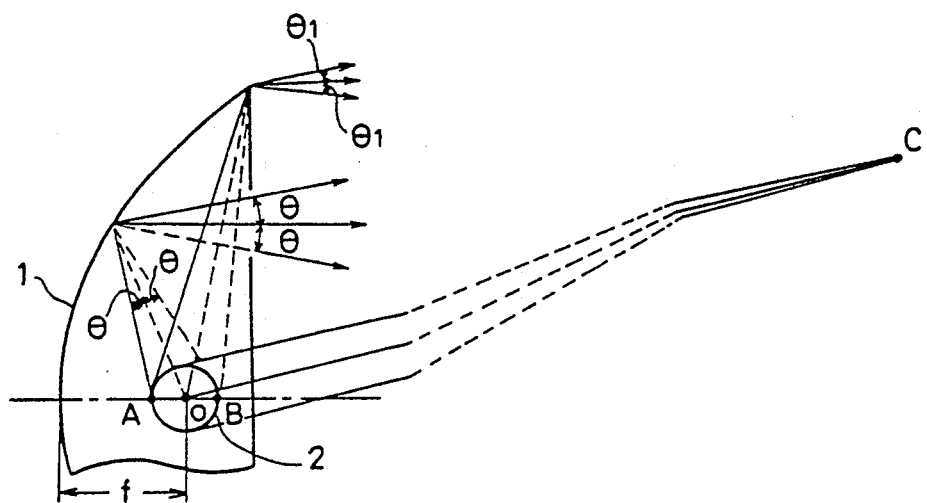
FIG. 1 is a schematic view of the prior art.
Figure 2:
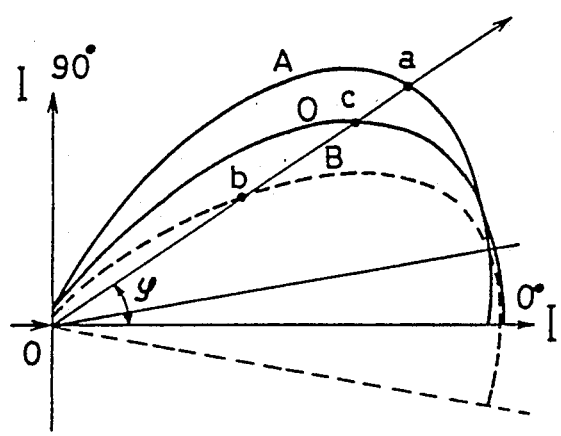
FIG. 2 is a graph illustrating the relation between the direction of light emitted from the points A and B and the light amount thereof in the prior art.
Figure 3:
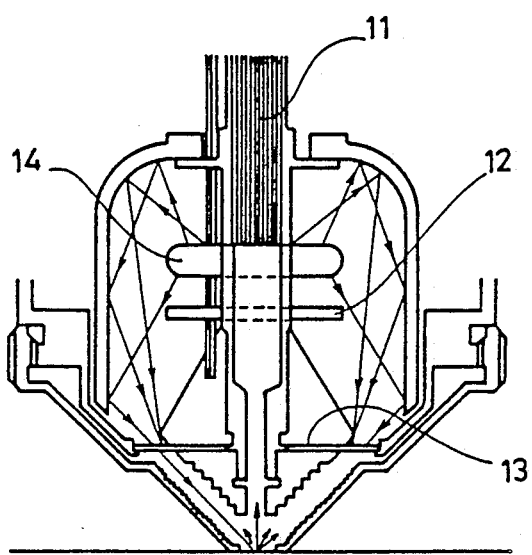
FIG. 3 is a vertical sectional view of a conventional colorimeter.
Figure 4:
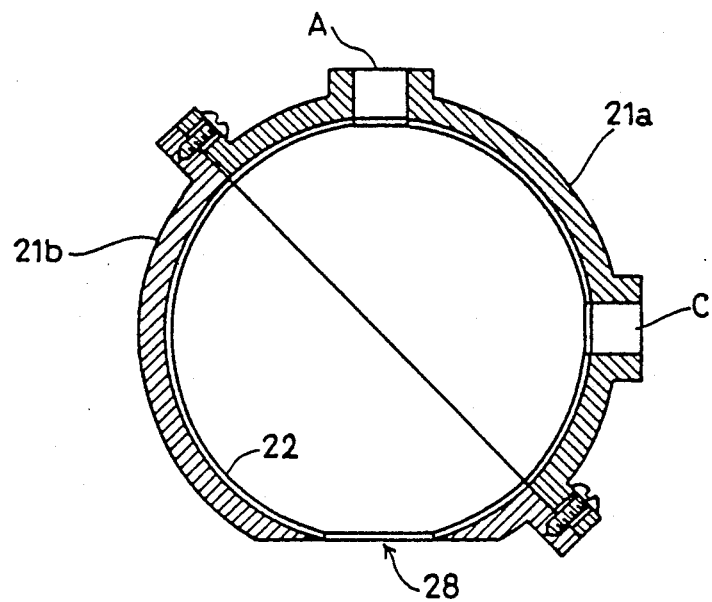
FIG. 4 is a vertical sectional view of another example of the prior art.
Figure 5:
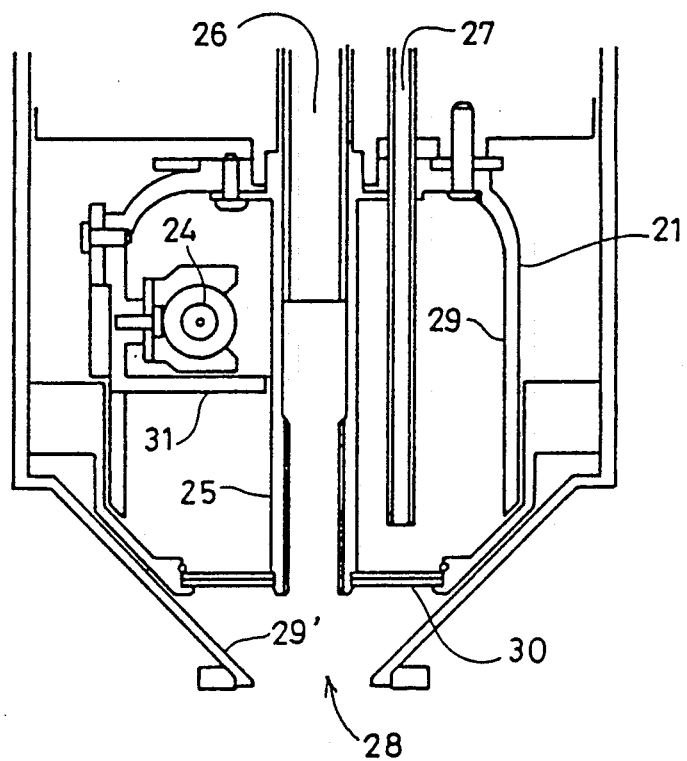
FIG. 5 is a vertical sectional view of a further example of the prior art.
Figure 6:
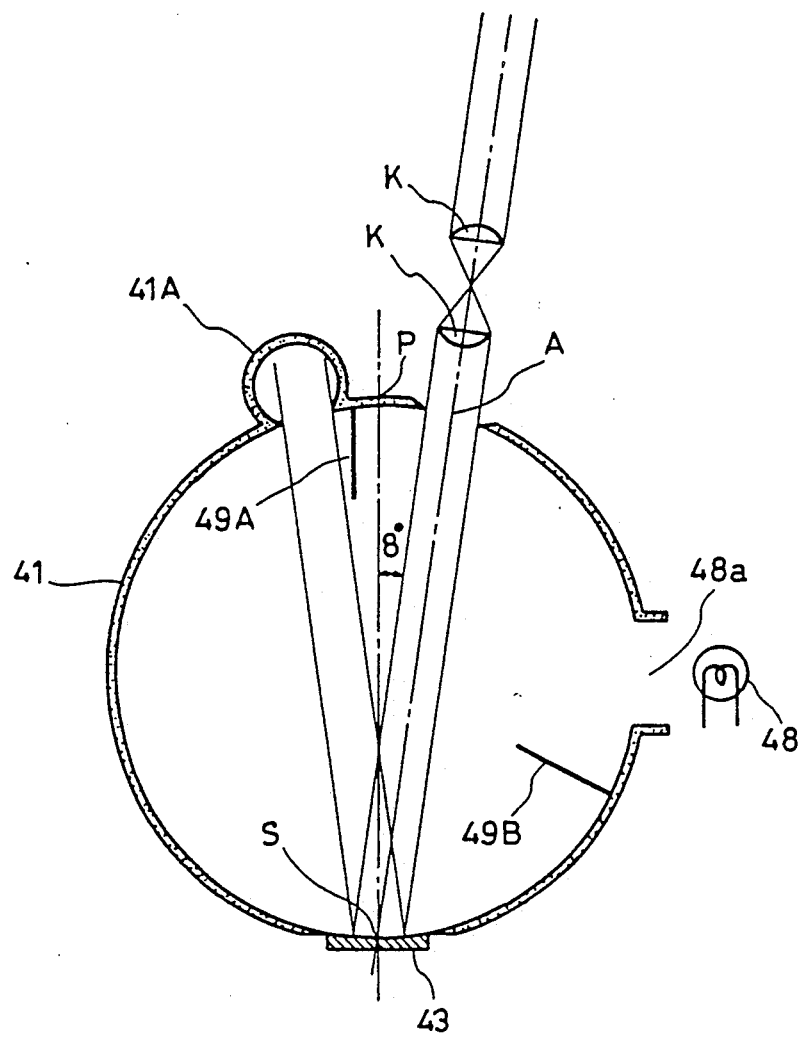
FIG. 6 is a vertical sectional view of a still further example of the prior art.
Figure 7:
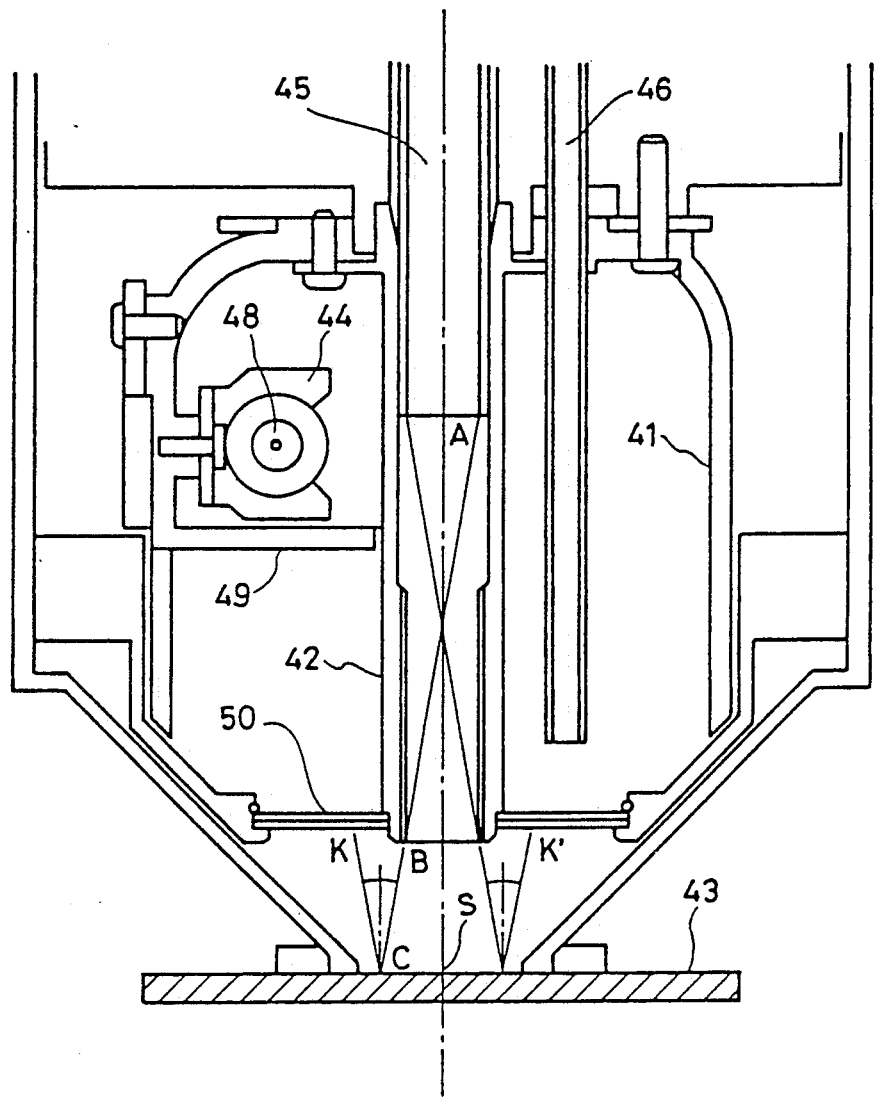
FIG. 7 is a vertical sectional view of a still further example of the prior art.
Figure 8:
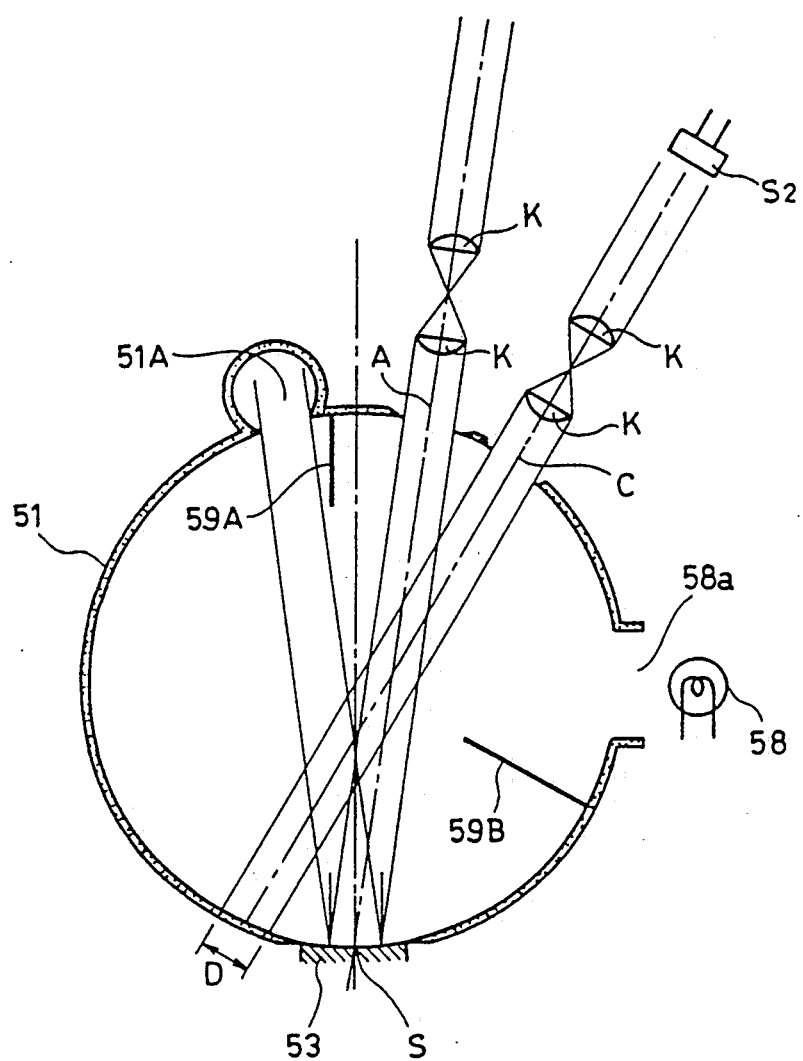
FIG. 8 is a vertical sectional view of a still further example of the prior art.
Figure 16:
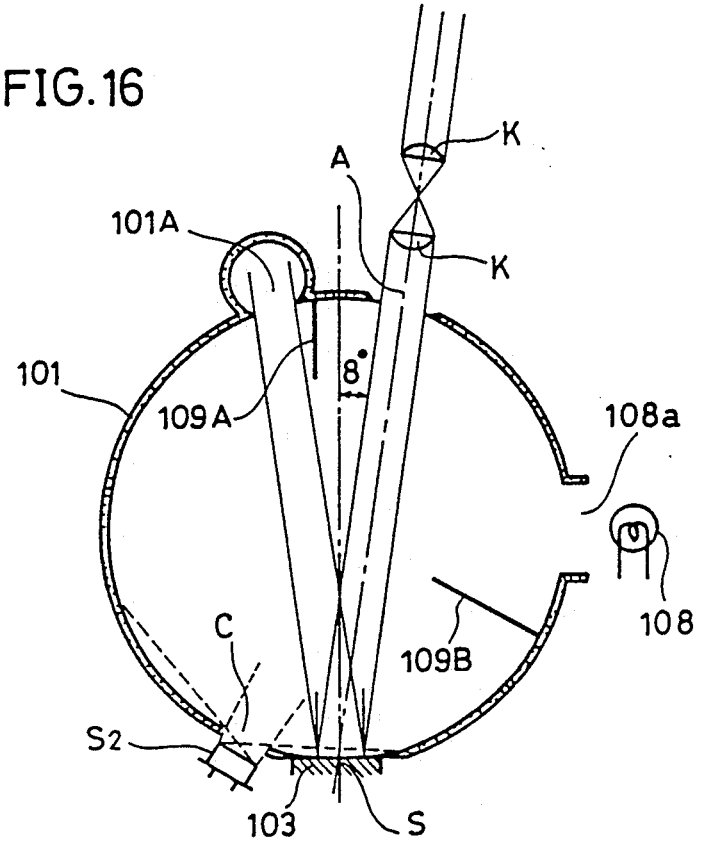
FIG. 16 is a vertical sectional view of a still further embodiment.

FIG. 16 shows one embodiment of the present invention which is a modification of the integrating sphere of the conventional type shown in FIG. 8. The amount of light which passes through the reference opening C to the sensor S2 for receiving the monitor light is almost the same as the whole amount of light entering the reference opening C. The area of the prior art shown in FIG. 8 which reflects the light entering the reference opening is the same as that of the reference opening C of this embodiment. Meanwhile, the inner surface of the integrating sphere 101 viewed from the reference opening C is almost the whole inner surface of the integrating sphere in the present invention. Therefore, when compared with the light amount of the prior art of FIG. 8, the light received by the sensor S2 is greatly increased.

The color measuring circuit of the colorimeter employing the integrating sphere of the embodiments is the same as that shown in FIG. 14.

In accordance with the present embodiments, the specular light reflected from the sample can be prevented without using a collimate lens or the like, whereby the apparatus can be made compact and less expensive. In addition, since the monitor light sensor receives the light reflected from almost all regions in the integrating sphere, the amount of monitor light can be enhanced and the precision in measurement is considerably enhanced.

Figure 17:
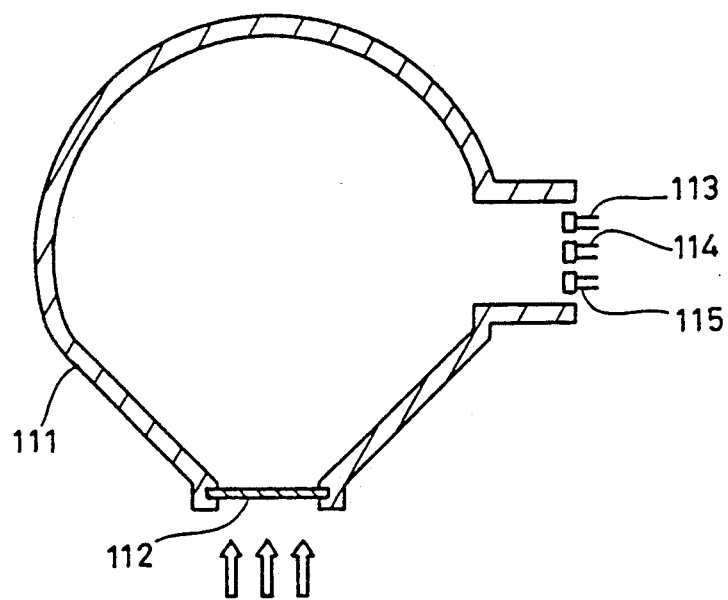
FIG. 17 is a vertical sectional view showing an example of application of the present invention.

Although the above described embodiments are related to the integrating sphere for obtaining diffusion illumination light in the diffusion illumination/vertical light receiving optical system, the present invention may be applied to an integrating sphere for receiving diffusion light in a vertical illumination/diffusion light receiving system. The present invention may be applied to mixing boxes other than the integrating sphere. The embodiment shown in FIG. 17 is a color analyzer for measuring the color of the light source, employed for the color measurement of a color CRT, for example. In FIG. 17, 111 denotes a mixing box, 112 denotes a diffusing plate, 113 denotes a red sensor, 114 denotes a green sensor and 115 denotes a blue sensor. In this color analyzer, the sample light is mixed by the plate 112, so that uniform light enters three sensors even if the sample light is uneven as in the case of the color CRT.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A colorimeter for measuring color of a sample, comprising:
    a light source;
    a mixing box formed of a non-coated light diffusing surface by molding.sintering white ceramics or white resin for diffusing and reflecting light from said light source to guide the same to said sample;
    first light receiving means for receiving light reflected from the sample when light is emitted from said light source; and
    second light receiving means for receiving light other than the light directly reflected from the sample when light is emitted from said light source.

2. A colorimeter according to claim 1, wherein said light source is a flash apparatus having a reflector having a concave non-coated light diffusing surface formed by molding.sintering white ceramics or white resin.

3. A colorimeter according to claim 1, wherein said first light receiving means is a cylinder projected into the mixing box from the upper surface of the mixing box,
    said cylinder having a portion for limiting a region to be color measured, a light receiving opening provided at an inner surface of said cylinder, and a collar portion provided at the outer periphery of said cylinder,
    a surface of said collar which is opposed to the sample being subjected to the light absorbing treatment, and said inner surface of said cylinder being subjected to the light absorbing treatment.

4. A colorimeter according to claim 1, wherein said mixing box comprises a sample opening and said second light receiving means comprises a measuring opening arranged adjacent to said sample opening.

5. A colorimeter of a diffused illumination.vertical light receiving system, comprising:
    a mixing box; and
    a cylinder projected into the mixing box from the upper surface of the mixing box, wherein said cylinder comprises an opening for limiting a region to be color measured at an opening portion at the end of the projection into the mixing box, a light receiving opening provided in the cylinder, and a collar portion provided at the outer periphery;
    the inner surface of said cylinder being subjected to light absorbing treatment and,
    a surface of said collar portion which is opposed to the sample being subjected to light absorbing treatment.

6. A mixing box comprising non-coated light diffusing surface formed by molding.sintering white ceramics or white resin.

7. A mixing box according to claim 6, wherein the white ceramics is aluminum oxide or boron nitride.

8. A mixing box according to claim 6, wherein said white resin is tetrafluoroethylene.

9. A reflector for a flash apparatus comprising concave non-coated light diffusing surface formed by molding.sintering white ceramics or white resin.

10. A reflector according to claim 9, wherein said white ceramics is aluminum oxide or boron nitride.

11. A reflector according to claim 9, wherein said white resin is tetrafluoroethylene.

* * * * *